United States Patent
Young et al.

(10) Patent No.: US 10,058,584 B2
(45) Date of Patent: Aug. 28, 2018

(54) METHODS OF IMPROVING BEHAVIORAL THERAPIES

(71) Applicant: Emory University, Atlanta, GA (US)

(72) Inventors: Larry James Young, Decatur, GA (US); Meera E. Modi, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/724,513

(22) Filed: Oct. 4, 2017

(65) Prior Publication Data
US 2018/0042985 A1    Feb. 15, 2018

Related U.S. Application Data

(60) Division of application No. 14/017,423, filed on Sep. 4, 2013, now Pat. No. 9,789,155, which is a continuation of application No. 13/111,293, filed on May 19, 2011, now abandoned.

(60) Provisional application No. 61/346,730, filed on May 20, 2010.

(51) Int. Cl.
*A61K 38/00* (2006.01)
*A61K 38/08* (2006.01)
*A61K 31/506* (2006.01)
*A61K 38/34* (2006.01)

(52) U.S. Cl.
CPC ............ *A61K 38/08* (2013.01); *A61K 31/506* (2013.01); *A61K 38/34* (2013.01)

(58) Field of Classification Search
None
See application file for complete search history.

(56) References Cited

PUBLICATIONS

Fan et al., Nature, 1997, 385:165-8.*

* cited by examiner

*Primary Examiner* — Olga N Chernyshev
(74) *Attorney, Agent, or Firm* — Emory Patent Group

(57) ABSTRACT

This disclosure provides methods of using compounds that act to increase oxytocin release, including certain melanocortin receptor agonists, for treating or reducing the severity of psychotherapeutic or social disorders such as autism, and in particular the use of these compounds as an adjunct to psychotherapeutic counseling or behavioral therapy.

5 Claims, 1 Drawing Sheet
Specification includes a Sequence Listing.

SEQUENCE LISTING

```
<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Ser Tyr Ser Met Glu His Phe Arg Trp Gly Lys Pro Val
1               5                   10

<210> SEQ ID NO 2

<400> SEQUENCE: 2

000

<210> SEQ ID NO 3
<211> LENGTH: 4
<212> TYPE: PRT
<213> ORGANISM: Artificial Sequence
<220> FEATURE:
<223> OTHER INFORMATION: Synthetic construct

<400> SEQUENCE: 3

His Phe Arg Trp
1

<210> SEQ ID NO 4
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X  represents Norleucine
<220> FEATURE:
<221> NAME/KEY: MOD_RES
<222> LOCATION: (3)..(3)
<223> OTHER INFORMATION: where His is D-HIS
<220> FEATURE:
<221> NAME/KEY: MOD_RES
<222> LOCATION: (4)..(4)
<223> OTHER INFORMATION: where Phe is D-Phe

<400> SEQUENCE: 4

Xaa Asp His Phe Arg Trp Lys
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic constructs
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
```

```
<400> SEQUENCE: 5

Xaa Asp His Phe Arg Trp Lys
 1               5

<210> SEQ ID NO 6
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: where His is D-His
<220> FEATURE:
<221> NAME/KEY: MOD_RES
<222> LOCATION: (4)..(4)
<223> OTHER INFORMATION: where Trp is D-Trp

<400> SEQUENCE: 6

His Phe Arg Trp
 1

<210> SEQ ID NO 7
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe

<400> SEQUENCE: 7

Xaa Asp His Phe Lys Trp Lys
 1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe

<400> SEQUENCE: 8

Xaa Asp Trp Phe Arg Trp Lys
 1               5

<210> SEQ ID NO 9
```

```
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (5)..(5)
<223> OTHER INFORMATION: where Arg is D-Arg

<400> SEQUENCE: 9

Xaa Asp Asp His Phe Arg Trp Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (6)..(6)
<223> OTHER INFORMATION: where Trp is D-Trp

<400> SEQUENCE: 10

Xaa Asp His Phe Arg Trp Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: an aminohexanoic acid at this location
<220> FEATURE:
<221> NAME/KEY: MOD_RES
<222> LOCATION: (3)..(3)
<223> OTHER INFORMATION: where Phe is D-Phe

<400> SEQUENCE: 11

Asp His Phe Arg Trp Lys
1               5

<210> SEQ ID NO 12
```

```
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe

<400> SEQUENCE: 12

Xaa Asp Tyr Phe Arg Trp Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe( (4-Cl)

<400> SEQUENCE: 13

Xaa Asp His Phe Arg Trp Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (5)..(5)
<223> OTHER INFORMATION: where n is Ornithine

<400> SEQUENCE: 14

Xaa Asp His Phe Asn Trp Lys
1               5

<210> SEQ ID NO 15
```

<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Where X is Nle
<220> FEATURE:
<221> NAME/KEY: MOD_RES
<222> LOCATION: (4)..(4)
<223> OTHER INFORMATION: Where Phe is D-Phe

<400> SEQUENCE: 15

Xaa Asp His Phe Arg Trp Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: Where Phe is D-Phe
<220> FEATURE:
<221> NAME/KEY: MOD_RES
<222> LOCATION: (6)..(6)
<223> OTHER INFORMATION: where n is 1-Naphthylalanine

<400> SEQUENCE: 16

Xaa Asp His Phe Arg Asn Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (6)..(6)
<223> OTHER INFORMATION: where n is biphenylalanine
<220> FEATURE:
<221> NAME/KEY: MOD_RES
<222> LOCATION: (6)..(6)
<223> OTHER INFORMATION: where X is biphenylalanine

<400> SEQUENCE: 17

Xaa Asp His Phe Arg Xaa Lys

-continued

```
<210> SEQ ID NO 18
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: X is succinic acid
<220> FEATURE:
<221> NAME/KEY: MOD_RES
<222> LOCATION: (3)..(3)
<223> OTHER INFORMATION: Where Phe is D-Phe

<400> SEQUENCE: 18

Xaa His Phe Arg Trp Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (6)..(6)
<223> OTHER INFORMATION: where Trp is D-Trp
<220> FEATURE:
<221> NAME/KEY: MOD_RES
<222> LOCATION: (7)..(7)
<223> OTHER INFORMATION: AMIDATION at this location

<400> SEQUENCE: 19

Xaa Gln His Phe Arg Trp Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: cyclohexy at this location
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (6)..(6)
<223> OTHER INFORMATION: where Trp is D-Trp
```

```
<220> FEATURE:
<221> NAME/KEY: MOD_RES
<222> LOCATION: (7)..(7)
<223> OTHER INFORMATION: AMIDATION at this location

<400> SEQUENCE: 20

Gly Gln His Phe Arg Trp Gly
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (2)..(2)
<223> OTHER INFORMATION: Where Phe is D-Phe
<220> FEATURE:
<221> NAME/KEY: MOD_RES
<222> LOCATION: (4)..(4)
<223> OTHER INFORMATION: Where Trp is D-Trp
<220> FEATURE:
<221> NAME/KEY: MOD_RES
<222> LOCATION: (4)..(4)
<223> OTHER INFORMATION: AMIDATION at this location

<400> SEQUENCE: 21

His Phe Arg Trp
1

<210> SEQ ID NO 22
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Where Phe is D-Phe
<220> FEATURE:
<221> NAME/KEY: MOD_RES
<222> LOCATION: (4)..(4)
<223> OTHER INFORMATION: Where Trp is D-Trp

<400> SEQUENCE: 22

His Phe Arg Trp Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (2)..(2)
<223> OTHER INFORMATION: where Phe is D-Phe
<220> FEATURE:
<221> NAME/KEY: MOD_RES
<222> LOCATION: (4)..(4)
<223> OTHER INFORMATION: where Trp is D-Trp
```

```
<220> FEATURE:
<221> NAME/KEY: MOD_RES
<222> LOCATION: (4)..(4)
<223> OTHER INFORMATION: AMIDATION at this location

<400> SEQUENCE: 23

His Phe Arg Trp Gly
1               5

<210> SEQ ID NO 24
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (13)..(13)
<223> OTHER INFORMATION: AMIDATION at this location

<400> SEQUENCE: 24

Ser Tyr Ser Met Glu His Phe Arg Trp Gly Lys Pro Val
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: where X is Nle
<220> FEATURE:
<221> NAME/KEY: MOD_RES
<222> LOCATION: (4)..(4)
<223> OTHER INFORMATION: Where Phe is D-Phe
<220> FEATURE:
<221> NAME/KEY: MOD_RES
<222> LOCATION: (7)..(7)
<223> OTHER INFORMATION: AMIDATION at this location

<400> SEQUENCE: 25

Xaa Asp His Phe Arg Trp Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Butir at this location
<220> FEATURE:
<221> NAME/KEY: MOD_RES
<222> LOCATION: (2)..(2)
<223> OTHER INFORMATION: where Phe is D-Phe
<220> FEATURE:
<221> NAME/KEY: MOD_RES
<222> LOCATION: (5)..(5)
<223> OTHER INFORMATION: where x is Sar
```

```
<220> FEATURE:
<221> NAME/KEY: MOD_RES
<222> LOCATION: (5)..(5)
<223> OTHER INFORMATION: AMIDATION at this location

<400> SEQUENCE: 26

His Phe Arg Trp Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION at this location
<220> FEATURE:
<221> NAME/KEY: MOD_RES
<222> LOCATION: (1)..(1)
<223> OTHER INFORMATION: where x is Nle
<220> FEATURE:
<221> NAME/KEY: MOD_RES
<222> LOCATION: (4)..(4)
<223> OTHER INFORMATION: where Phe is D-Phe
<220> FEATURE:
<221> NAME/KEY: MOD_RES
<222> LOCATION: (9)..(9)
<223> OTHER INFORMATION: AMIDATION at this location

<400> SEQUENCE: 27

Xaa Asp Pro Phe Arg Trp Lys Pro Val
1               5
```

METHODS OF IMPROVING BEHAVIORAL THERAPIES

CROSS-REFERENCE TO RELATED APPLICATIONS

This application is a division of U.S. application Ser. No. 14/017,423 filed Sep. 3, 2013, which is a continuation of U.S. application Ser. No. 13/111,293 filed May 19, 2011, which claims the benefit of priority to U.S. Provisional Application No. 61/346,730 filed May 20, 2010. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 09167USDIV_ST25.txt. The text file is 11 KB, was created on Oct. 3, 2017, and is being submitted electronically via EFS-Web.

FIELD

This disclosure describes the use of certain compounds that act to increase brain oxytocin release for improving behavior and social cognition in certain psychiatric disorders, and as an adjunct to psychotherapeutic behavioral counseling, therapy, and emotional recovery associated, but not limited to, the treatment of mental health disorders and conditions.

BACKGROUND

Certain behavioral disorders are largely treated with psychological counseling or behavioral therapies, such as certain addictions, obsessive-compulsive disorder, Tourette's syndrome, autism spectrum disorder, schizophrenia, post-traumatic stress disorder (PTSD), anxiety disorders, and other disorders involving troubling memories. Even in disorders for which pharmaceutical treatment is available, such as bipolar disorder, depression, and schizophrenia, counseling is used as an adjunct.

Behavioral disorders are difficult to treat and often result in relapse. A number of behavioral disorders have been treated with varying degrees of success by repeatedly exposing patients to situations that elicit symptoms of these disorders. Drug and alcohol addiction have been treated with limited success using a "cue elicited craving paradigm" which involves presenting addicts with drug-related cues (e.g., videotapes, audiotapes, actors performing simulated drug administration rituals, pictures or slides of white powder, crack pipes, bar scenes, etc.) designed to elicit craving. This exposure treatment aims to reduce the tendency for patients to respond to these situations.

Animal models of anxiety disorders have been used to screen for drugs that promote the reduction of conditioned fear. For example, D-cycloserine, a drug that promotes NMDA receptor activity, was found to facilitate the reduction of conditioned fear (Davis et al., Biol. Psychiatry 51:1S, 2002; Walker et al., J. Neurosci. 22:2343-2351, 2002). However, an obstacle for this treatment approach is that symptoms of anxiety disorders can show resistance to extinction (Poulton R, et al. Behav. Res. Ther. 39:29-43, 2001; Poulton R and Menzies R G. Res. Ther. 40:197-208, 2002). Repetitive transcranial magnetic stimulation (rTMS) was also developed as a noninvasive method of altering the excitability of neuronal circuitry in the brain. Preliminary studies of patients with focal dystonia, epilepsy, PTSD, depression, or schizophrenia have revealed modest symptom reductions after rTMS treatment.

Oxytocin (OT) has also been implicated as a potential factor in certain psychiatric disorders. For example, based on a review of evidence from animal studies demonstrating that altered OT and vasopressin have unique effects on the normal expression of species-typical social behavior, communication, and rituals, Insel and colleagues have proposed that altered OT or vasopressin neurotransmission may account for several features associated with autism. See Insel et al., Biol. Psychiatry 45:145-157, 1999. A study on autistic children reported that such children had significantly lower levels of plasma OT than normal children. Elevated OT levels were associated with higher scores on social and developmental tests in non-autistic children, but associated with lower scores in autistic children, suggesting that altered OT levels may be associated with autism in children (Modahl et al., Biol. Psychiatric 43:270-277, 1998). A role for OT in obsessive compulsive disorders has also been proposed (Leckman et al., Psychoneuroendocrinology 19:723-749, 1994; but see Altemus et al., Biol. Psychiatry 45:931-33, 1999, see also U.S. Patent Publication 2006/0105939).

In particular, elevated levels of OT have been proposed to affect certain obsessive-compulsive behaviors, such as excessive worrying, sexual compulsions and/or compulsive washing and cleaning. (Leckman et al., Psychoneuroendocrinology 19:723-749, 1994; Leckman et al., Arch Gen Psychiatry 51:782-92, 1994). Elevated levels of OT have also been implicated in Prader-Willi syndrome, a genetic disorder associated with mental retardation, appetite dysregulation, and a risk of developing obsessive compulsive disorder (Martin et al., Biol. Psychiatric 44:1349-1352, 1998).

Elevated levels of the peptide OT have been associated with the onset of pro-social behaviors. Exogenously administered OT enhances prosocial behavior and social information processing in animal models, and intranasal OT enhances some aspects of social cognition in humans suggesting that the OT system may be a viable target for pharmacological therapies for disorders characterized by social deficits, like autism spectrum disorders and schizophrenia. In non-clinical populations, intranasal OT has been shown to increase trust, generosity, empathy, socially reinforced learning, (Hurlemann et al, 2010 J. Neurosci., 30:4999) and attention to and comprehension of emotional expression. Administration of intranasal OT to individuals with autism spectrum disorder, has recently been found to increase social interactions and feelings of trust toward cooperative individuals and time spent gazing at the eye region of a social partner in a social cooperative game (Andari et al., Proc Natl Acad Sci USA, 2010, 107:4389-4394) and to increase the ability to interpret emotional expression (Guastella et al., Biol Psychiatry, 2008, 63:3-5). References cited herein are not an admission of prior art.

Social bonding in voles is a useful behavioral paradigm to assess the social cognitive enhancement properties of drugs. OT appears to increase the saliency of social stimuli and to enhance social information processing, and may also tag social stimuli with a reinforcing state. OT also has a role in decreasing anxiety-like and anxiety behaviors. In humans, nasal OT administration has been shown to decrease the level of the stress hormone cortisol and enhance positive behavioral aspects. OT dysfunction has been implicated in schizophrenia. Patients with schizophrenia have been shown to have a decreased level of OT in their blood.

Intravenous OT administration has resulted in modest behavioral effects in individuals with autism spectrum disorder (ASD) as only a small fraction of the peptide is able to cross the blood-brain-barrier due to the poor permeability of the peptide. Neuropharmacological studies have recently suggested that OT gains better access to the brain through intranasal administration. Though, while many behavioral studies have been conducted using this technique, no study to date has shown an increase in central OT levels following intranasal dosing.

Although administration of OT has been attributed positive mood in humans, OT is a large peptide that does not effectively cross the blood brain barrier. Because OT does not cross be blood brain barrier effectively, there is a need to develop a more efficient means of increasing the levels and effectiveness of OT in the brain.

A number of OT analogs have been evaluated, largely as possible substitute agents for inducing uterine contraction and milk let-down, rather than to enhance brain penetration and activity (Atke et al., Acta Endocrinol. 115:155-160, 1987; Norstrom et al., Acta Endocrinol. 122:566-568, 1990; Hunter et al., Clin. Pharmacol. Ther. 52:60-67, 1992; Silcox et al., Obstet Gynecol. 82:456-459, 1993; Vilhardt et al., Pharmacol. Toxicol. 81:147-150, 1997; Boucher et al., J. Perinatology 18:202-207, 1998).

Melanocortin receptors are localized on OT neurons, and stimulation of these receptors has been shown to stimulate the release of oxytocin within the brain (Sabatier et al., J Neuroscience, 2003, 23(32):10351-10358). Melanocortin receptor-specific compounds have been explored for use of treatment of sexual dysfunction. A cyclic melanocyte-stimulating hormone ("alpha-MSH") analog, called Melanotan-II, was evaluated for erectogenic properties for the treatment of men with psychogenic erectile dysfunction. OT also has erectogenic properties, and the release of OT may be one mechanism underlying this effect of MTII. Wessells et al., J Urology 160:389-393 (1998); see also U.S. Pat. Nos. 5,576, 290 and 6,051,555. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled Cyclic Analogs of Alpha-MSH Fragments, and in U.S. Pat. No. 5,714,576, issued Feb. 3, 1998, to V. J. Hruby, M. E. Hadley and F. Al-Obeidi, entitled Linear Analogs of Alpha-MSH Fragments. Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. These peptides are related to the structure of melanocortins. Other peptides are disclosed in U.S. Pat. Nos. 6,284,735 and 4,649,191, and U.S. Published Patent Applications Nos. 2001/0056179 and 2002/0004512.

There remains a need for improved therapeutic modalities for treatment of behavioral disorders. It is an object of this disclosure to provide treatment methods for improving the outcome of therapeutic treatments of a behavioral disorder. It is a further object of the disclosure to provide a method of mood elevation and enhancement of social cognition in a subject in need thereof.

SUMMARY

It is contemplated that drugs that stimulate the release of OT will enhance trust, social information processing, empathy and general social cognitive function during behavioral therapy or counseling sessions, e.g. during marital therapy, thereby increasing their efficacy of these sessions.

In certain embodiments, the disclosure contemplates the use of oxytocin-releasing agents in combination with applied behavior analysis and reinforcing stimuli for behavioral training.

In certain embodiments, the disclosure relates to methods of improving social cognition in a subject in need thereof including administering a compound that stimulates oxytocin (OT) release in the brain. Typically, the compound that stimulated OT release is a melanocortin receptor agonist. The compound, in certain embodiments, is melanotan II or derivative thereof.

In certain embodiments, the disclosure relates to methods of improving the efficacy of psychotherapeutic treatment comprising administering a pharmaceutical composition comprising an oxytocin releasing agent to a subject diagnosed with a psychiatric or behavioral disorder. Typically, the administration is about the time period that behavioral psychotherapeutic counseling is being administered.

In specific embodiments, the disclosure relates to methods for treating a psychological disorder including administering a compound that stimulates OT release to a subject in conjunction with psychotherapeutic counseling or behavioral therapy. It is believed that the release of OT will enhance the efficacy of the psychotherapeutic counseling or behavioral therapy by enhancing social cognitive functioning of the patient. In certain embodiments, the compound is administered within a psychotherapeutic window. The psychotherapeutic window can be within one month of a psychotherapy session, or within one week of a psychotherapy session, or within one day of a psychotherapy session. The compound can be administered during the therapy session, and in certain embodiments, is administered before the session begins. The oxytocin-releasing drug may be administered by a clinician. Alternatively, the drug may be self-administered by the patient. The oxytocin-releasing drug is typically administered within five hours of a psychotherapy session. In one embodiment the drug is administered within five minutes of a psychotherapy session. However, in an alternative embodiment the drug is administered up to one hour prior to a psychotherapy session. The therapy may be administered acutely or as a chronic regimen.

In certain embodiments, the compounds that promote oxytocin release promote the onset of positive emotional mood without systemic effects on the oxytocin system. Typically, the compounds do not cause increases in heart rate, blood pressure, motor activity.

The psychiatric disorder can include, but is not limited to, a disorder selected from the group consisting of depression, bi-polar disorders, anxiety disorders, panic attacks, agoraphobia, attention deficit syndrome, mid-cycle dysphoria, premenstrual dysphoric disorder (PMDD), and premenstrual syndrome (PMS), autism spectrum disorder (ASD), addiction, obsessive-compulsive disorder, Tourette's Syndrome, post-traumatic stress disorder (PTSD), bipolar disorder, depression, schizophrenia, and personality disorders.

In one aspect, the present disclosure provides a method of treating a behavioral disorder comprising presenting a cue associated with the disorder to a patient in combination with administering an oxytocin-releasing drug to the patient. This may be repeated as needed to alleviate symptoms of the disorder. The alleviation of symptoms may be measured by a clinician using standard techniques. The cue is preferably at least one of a visual, olfactory, aural, tactile, or gustatory cue. It may be presented in a clinical environment or as part of the patient's natural environment outside of the clinic.

In one aspect, the present disclosure provides methods for treating behavioral disorders by combining behavioral reinforcement in combination with administering an oxytocin-releasing agent to a subject in need thereof.

The compound is preferably administered in an amount ranging from about 0.001 to 10 microgram per day and is preferably formulated in a liquid vehicle and provided at a concentration of approximately 0.04 micrograms as a single drop. A single drop of oxytocin releasing compound is within the range of 0.001 to 1 microgram. The composition is typically administered in an amount ranging from about 0.05 to 1 microgram per day or from about 0.01 to 0.1 micrograms per day. In typical embodiments, the compound is administered orally in the form of a pill, via nasal, ocular or intravenous method.

In certain embodiments, a method of treatment or prophylaxis of autism or an autistic spectrum disorder is provided including administering a compound that increases oxytocin release, and in particular which is a melanocortin receptor agonist to a subject in need thereof. The compound, in certain embodiments, is melanotan II or derivative thereof. In other embodiments, the oxytocin releasing agent is a serotonin receptor agonist, and in particular embodiments, it is a 5-HT 1a or 5-HT 2a/c agonist such as buspirone, gepirone, tandospirone serotonin, ergine, ergotamine, lysergic acid, lysergic acid diethylamide, psilocybin, 4-hydroxy-dimethyltryptamine, N,N-dimethyltryptamine, 5-methoxy-dimethyltryptamine, mescaline, 4-bromo-2,5-dimethoxyphenethylamine, 3,4-methylenedioxymethamphetamine, methylenedioxyethylamphetamine, tenamfetamine, lorcaserin, or salts thereof.

In certain embodiments, the subject has been diagnosed with autism or Asperger syndrome. In certain embodiments, the subject has been diagnosed with an autistic spectrum disorder. In certain embodiments, the subject is less than eighteen years old. In still further embodiments, the subject is less than thirteen years old. In certain embodiments, the subject is prepubescent. With certain embodiments, autism behavioral therapies are designed to submerse the patient in social stimuli and "train" the brain to function in a socially appropriate manner.

In certain embodiments, the disclosure relates to uses of compounds that increase brain oxytocin in combination with digital media, e.g., a computer program, game, or movie to increase social cognition.

Within any of the embodiments, disclosure herein a compound that increases oxytocin release may be a melanocyte stimulating hormone or analog such as a cyclic melanocyte-stimulating hormone, melanotan II, or bremelanotide or a peptide comprising sequence HFR (SEQ ID NO: 2) or HFRW (SEQ ID NO:3) or a peptide sequence having a D-amino acid, D-phenylalanine, phenylalanine with substituted with one or more halogens, or D-4-chlorophenylalanine. In certain embodiments, the analog is Ac-Nle-cyclo(-Asp-D-His-D-Phe-Arg-Trp-Lys)-OH (SEQ ID NO:4), Ac-Nle-cyclo(-Asp-His-Phe-Arg-Trp-Lys)-OH (SEQ ID NO:5), Ac-Nle-cyclo(-Asp-His-D-Phe-Lys-Trp-Lys)-OH (SEQ ID NO:7), Ac-Nle-cyclo(-Asp-Trp-D-Phe-Arg-Trp-Lys)-OH (SEQ ID NO:8), Ac-Nle-cyclo(-Asp-His-D-Phe-D-Arg-Trp-Lys)-OH (SEQ ID NO:9), Ac-Nle-cyclo(-Asp-His-D-Phe-Arg-D-Trp-Lys)-OH (SEQ ID NO:10), Ahx-cyclo(-Asp-His-D-Phe-Arg-Trp-Lys)-OH (SEQ ID NO:11), Ac-Nle-cyclo(-Asp-Tyr-D-Phe-Arg-Trp-Lys)-OH (SEQ ID NO:12), Ac-Nle-cyclo(-Asp-His-D-Phe(4-C1)-Arg-Trp-Lys)-OH (SEQ ID NO:13), Ac-Nle-cyclo(-Asp-His-D-Phe-Orn-Trp-Lys)-OH (SEQ ID NO:14), Nle-cyclo(-Asp-His-D-Phe-Arg-Trp-Lys)-OH (SEQ ID NO:15), Ac-Nle-cyclo(-Asp-His-D-Phe-Arg-Nal 1-Lys)-OH (SEQ ID NO:16), Ac-Nle-cyclo(-Asp-His-D-Phe-Arg-Bip-Lys)-OH (SEQ ID NO:17), or Cyclo(-Succ-His-D-Phe-Arg-Trp-Lys)-OH (SEQ ID NO:18) as disclosed in U.S. Pat. No. 7,176,279 or Ac-Nle-Gln-His-(D)Phe-Arg-(D)Trp-Gly-NH2 (SEQ ID NO:19), Ac-(cyclohexyl)Gly-Gln-His-(D)Phe-Arg-(D)Trp-Gly-NH2 (SEQ ID NO:20), Ac-His-(D)Phe-Arg-(D)Trp-NH2 (SEQ ID NO:21), cyclo(His-(D)Phe-Arg-(D)Trp) (SEQ ID NO: 6), cyclo(His-(D)Phe-Arg-(D)Trp-Gly) (SEQ ID NO:22), or Ac-His-(D)Phe-Arg-(D)Trp-Gly-NH2 (SEQ ID NO:23) as disclosed in U.S. Pat. No. 6,245,738.

In certain embodiments, the disclosure relates to methods of improving social attachment comprising administering a pharmaceutical composition comprising an oxytocin releasing agent to a subject undergoing marital counseling. Typically, the administration is about the time period that marital counseling is being administered.

DETAILED DESCRIPTION

Figure 1:
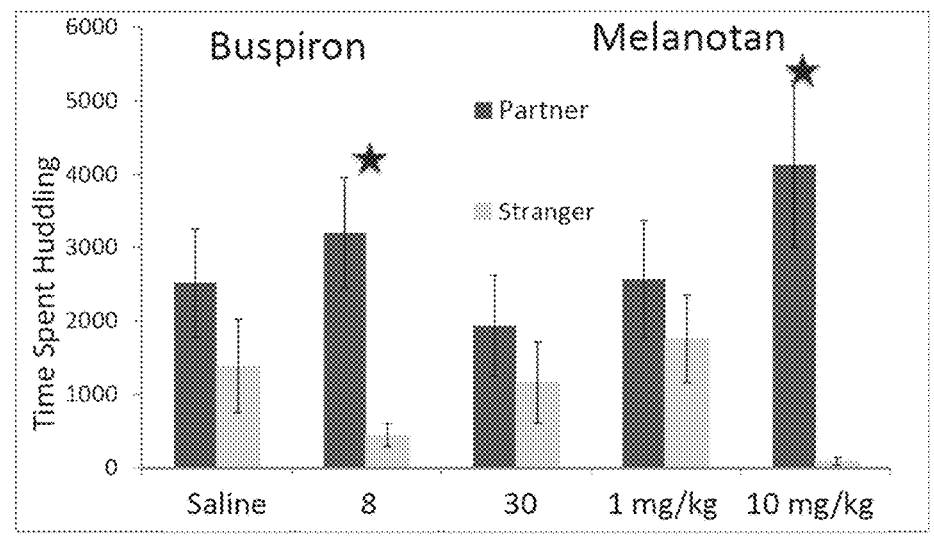
FIG. 1 shows data suggesting MTII I.P. administration promotes the formation of a partner preference in monogamous prairie voles following a 6 hour cohabitation period with a partner. Partner preference formation is a complex cognitive process that involves social motivation, social reward and social learning. Partner preference formation typically requires 24 hrs of cohabitation in the absence of mating. However, MTII and buspirone, a serotonin agonist that also stimulates oxytocin release, accelerates partner preference formation to 6 hrs or less. A partner preference is indicated when the subject spends more time huddling with the partner than a novel "stranger". Partner preference formation is considered a behavioral assay for social cognitive processes, and drugs that accelerate partner preference formation in voles may enhance social cognition in humans. Stars indicate a significant increase observed in time spent huddling between the pairing of familiar partners vs. unfamiliar stranger voles.
Figure 2:
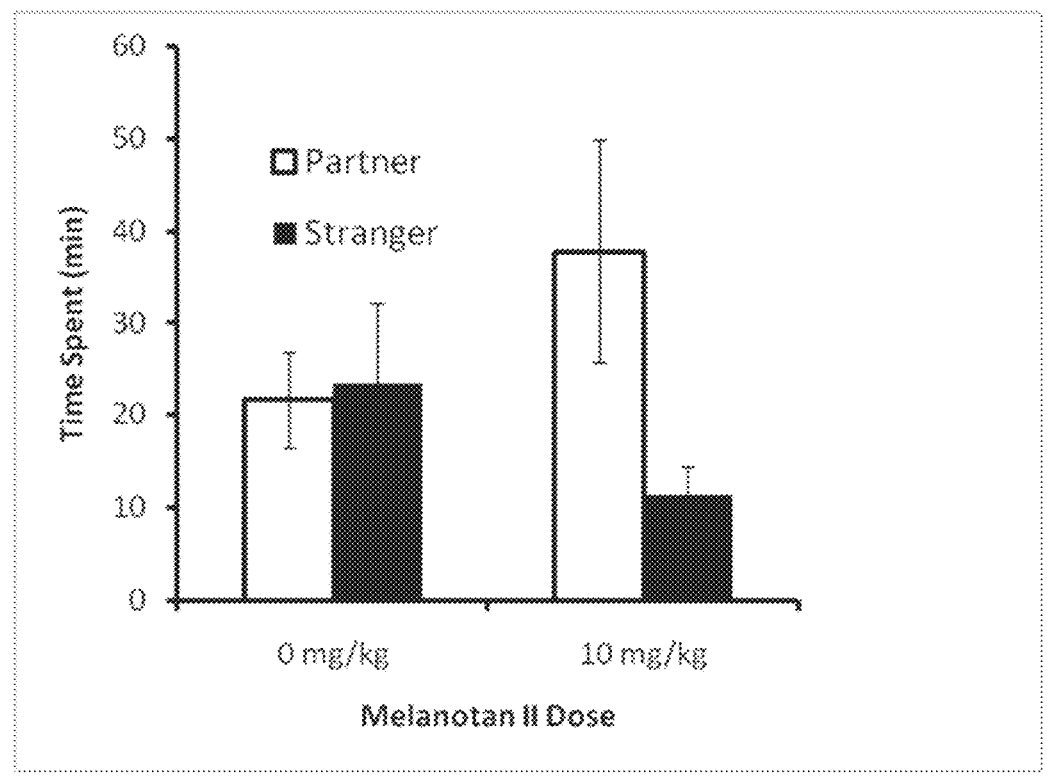
FIG. 2 shows data suggesting MT II facilitated the formation of social memories that endure well after the training.

All patents, patent applications, and publications cited herein are hereby incorporated by reference.

Melanocortins (MCs) constitute a family of proteins derived from the common precursor proopiomelanocortin (POMC). Prohormone-converting enzymes cleave POMC into several bioactive peptides including α-, β- and γ-melanocyte-stimulating hormone (MSH), adrenocorticotropic hormone (ACTH), and the opioid β-endorphin. The first two of these peptides interact with specific MC receptors (MCRs). Although five G-protein-coupled MCRs, named MC1-5, have been identified, only the MC3 and MC4 subtypes are believed to be expressed in the central nervous system. In certain embodiments, the melanocyte stimulating hormone or analog is a melanocotin receptor 4 (MC4) agonist. In certain other embodiments, the melanocyte stimulating hormone or analog is a melanocortin receptor 3 (MC3) agonists.

Melanocortins are a family of multifunctional peptidergic hormones. MCs are primarily known for their role in the regulation of adrenal steroid production and skin pigmentation, but the MC system is also involved in the modulation of a variety of other functions including fever, immunity and body weight homeostasis. The role of MC receptors in the regulation of male sexual behavior has received increasing attention. In the female rat, non-selective MC receptor agonists have been shown to increase lordosis, the dorsi-flexion of the back denoting female sexual receptivity.

As used herein, the terms "melanocyte stimulating hormone or analog" or "melanocortin receptor agonist" refer to a molecule, which can bind at least one melanocortin receptor such as *Homo sapiens* MC4R. Examples of other *Homo sapiens* melanocortin receptors include MCR1, MCR2, MCR3, and MCR5. A given peptide chain is a "melanocortin receptor" if it has at least 85% amino acid sequence identity to a known melanocortin receptor sequence or the mature form of a known melanocortin receptor and can function as a G-protein coupled receptor. Percent identity between two peptide chains can be determined by pairwise alignment using the default settings of the AlignX module of Vector NTI v.9.0.0 (Invitrogen Corp., Carlsbad, Calif.). An exemplary melanocyte stimulating hormone is the 13 amino acid alpha-MSH peptide having the amino acid sequence SYSMEHFRWGKPV (SEQ ID NO: 1). Other melanocyte stimulating hormones include biologically active fragments or derivatives of SEQ ID NO: 1 and other amino acid sequences that can bind a melanocortin receptor. The term "biologically active fragment" as used herein, refers to a portion of an alpha-MSH peptide that can bind to a melanocortin receptor such as MC4R. The peptide sequence HFRW (SEQ ID NO: 3) is an exemplary "biologically active fragment" of the alpha-MSH peptide sequence SYSMEHFRWGKPV (SEQ ID NO: 1). The HFRW fragment has been incorporated into the structure of the synthetic melanocortin receptor activator molecule melanotan II (MTII) (Fan et al., Nature 385: 165-168 (1997)).

Alpha melanocortin is a naturally occurring tridecapeptide which is believed to interact with numerous receptors to induce various pharmacological activities. Alpha-melanotropin, also known as α-MSH and α-melanocyte stimulating hormone, has the following formula: Ac-Ser-Tyr-Ser-Met-Glu-His-Phe-Arg-Trp-Gly-Lys-Pro-Val-NH2 (SEQ ID NO: 24). Where the peptide amino acid sequence are abbreviated as serine (Ser), Tyrosine (Tyr), methionine (Met), glutamic acid (Glu), histidine (His), arginine (Arg), glycine (Gly), lysine, (Lys), proline (Pro), valine (Val). An acyl group is abbreviated Ac and an amino group is abbreviated as (NH2).

Additional compounds useful in the present disclosure include PT-141, (bremelanotide) Ac-Nle-cyclo[Asp-His-D-Phe-Arg-Trp-Lys]-OH (SEQ ID NO: 7). Additional compounds useful for the present method include one or more of a melanocortin receptor agonist or modulator or melanocortin enhancer, such as melanotan II (Ac-Nle-cyclo[Asp-His-D-Phe-Arg-Trp-Lys]-NH$_2$) (SEQ ID NO: 25), PT-141 or compounds described in WO-09964002, WO-00074679, WO-09955679, WO-00105401, WO-00058361, WO-00114879, WO-00113112, WO-09954358. Giuliani et al., (2007) Br. J. Pharmacol. 150:595-603 described certain selective MC4 receptor agonists including Butir-His-D-Phe-Arg-Trp-Sar-NH2 (R027-3225) (SEQ ID NO: 26), Ac-Nle-c[Asp-Pro-D-Phe-Arg-Trp-Lys]-Pro-Val-NH2 (PG-931) (SEQ ID NO: 27) and [Nle4, D-Phe7]α-MSH (NDP-α-MSH). Further, the peptide HS024 is available and can be purchased from Neosystem (Strasbourg, France). Dyck et al. (2003) Bioorg. Med. Chem. Ltr. 13:3793-3796 described certain aryl piperazine melanocortin MC4 receptor agonists. In some embodiments, the compound is an MC3 receptor agonists such as gamma-MSH.

Conjugate molecules are also contemplated for uses disclosed herein such as those described in U.S. Pat. No. 7,910,101. A conjugate molecule may comprises a melanocortin receptor agonist, with a linking polypeptide or chemical linkage to a portion of a C-terminus of an immunoglobulin variable region and/or a portion of an immunoglobulin variable hinge region and/or an immunoglobulin heavy chain constant region and or an immunoglobulin heavy chain constant region.

Alpha-MSH can enhance OT release from neurons. Alpha-MSH binds to the melanocortin 3 (MC3) and melanocortin 4 (MC4) receptors. Administration of alpha-MSH in hypothalamic neurons has been demonstrated to bind to MC4 receptors, enhancing calcium depolarization leading to the increase release of OT from dendrites on neurons. Furthermore, the half life of OT release following alpha-MSH administration is 20 minutes (Sabatier et al., J Neuroendocrinol, 2006, 18(9): 703-710). Although not intending to be bound by theory, Alpha-MSH is believed to act on the OT ergic neurons of hypothalamus to stimulate OT release. Intracerebroventricular injection of alpha-MSH induces expression of Fos, a neuronal marker of activation in the supraoptic nucleus (Sabatier et al., J Neuroscience 23, 2003, (12): 10351-10358). Application of the peptide or a specific MC4 agonist to isolated supraoptic nuclei preparations results in a substantial release of OT from the dendrites, while inhibiting peripheral axonal release. Peripheral release of OT, however, can be induced by 5-HT 1a and 5-HT 2a/c agonists.

Several prolonged acting, enzymatically resistant MC analogs have been designed and synthesized to determine the functional role of the MC receptors. Among these analogs, is the alpha MSH agonist melanotan-2 (MT II) (U.S. Pat. Nos. 4,485,039, 4,457,864, 6,054,556). MTII has been demonstrated as an effective tanning agent (U.S. Pat. Nos. 4,866,038, 4,918,055, 5,674,839), promotes weight loss and is a potent improver of erectile function in men and women.

Although a MTII administration has been implicated as a means for treating mental health disorders (WO/2009/033712), there are no indications that MTII administration has been utilized to improve the efficacy of psychotherapeutic treatment during the time period that behavioral psychotherapeutic counseling is being administered.

Pair bond formation in monogamous prairie voles is an oxytocin dependent processes that can be assessed in the laboratory using a partner preference paradigm. If a vole has formed a bond its partner, it will prefer to spend more time huddling with the partner than a novel individual. Without mating, female voles require 24 hrs or more of cohabitation with a male to display a partner preference. However, if OT is administered, the partner preference is formed in 6 hrs or less. Partner preference formation is a complex cognitive processes that requires social reward and reinforcement, social information processing, and social learning. These same processes are involved in many aspects of human social cognition, and are impaired in disorders such as autism spectrum disorder. One can consider the cohabitation paradigm as being analogous to a psychotherapy session, when a patient must learn from the social signals around him/her. Drugs that can accelerate partner preference formation therefore enhance the efficacy of psychotherapeutic counseling. Thus partner preference formation is a behavioral paradigm that may be useful in drug discovery for the treatment of disorders typically treated by psychotherapies and counseling. MT II has been shown to dramatically accelerate partner preference formation in prairie voles (See FIG. 1).

Methods of Treatment

The present disclosure provides methods for treatment of psychological conditions or psychiatric disorder in a patient, said method comprises administering to the patient a therapeutically effective amount of an oxytocin releasing compound in combination or alternation with psychotherapy. The term "psychiatric disorder" or "psychological condition" as used herein includes depression, hypomania, cyclothymia, anxiety, bipolar disorder, insomnia and other sleep disorders, hyperactivity, attention deficit disorder, chronic fatigue syndrome, fear and anxiety disorders such as panic disorder, specific phobia, posttraumatic stress disorder (PTSD), obsessive-compulsive disorder, and movement disorder such as Tourette's syndrome, addictive disorders including substance abuse disorders, and mood disorders. For purposes of the present disclosure, an individual may have a single disorder, or may have a constellation of disorders that are to be treated by the methods described herein.

The methods and compositions of the disclosure are also useful for the treatment or alleviation of symptoms of a psychiatric disorder in a mammalian patient, as well as for the prophylaxis of patients at risk for developing a psychiatric disorder. Subject patients for treatment according to the methods of the disclosure include males and females diagnosed with a psychiatric disorder, such as obsessive compulsive disorder, autism or Prader-Willi syndrome, or patients who have been treated for a known psychiatric disorder, and thus present an elevated risk of recurrence. For example, subject patients having obsessive compulsive disorder can be treated with an oxytocin releasing compound. Subject patients typically have a psychiatric disorder (e.g., autism or Prader-Willi syndrome) characterized by one or more obsessive-compulsive behaviors (e.g., excessive worrying, sexual compulsions and/or compulsive washing and cleaning) can be treated with an oxytocin releasing compound to alleviate the symptoms of the obsessive-compulsive behavior.

Subject patients for prophylactic therapy according to the methods of the disclosure include males and females who have a family history of a psychiatric disorder, or who have a genetic predisposition for developing the disorder (e.g., have markers indicating elevated risk for development of the disorder). Psychiatric disorder treatment and prevention employing the methods and compositions of the disclosure may be implemented as an independent treatment program or as a follow-up, adjunct or coordinate treatment regimen for patients suffering from such a disorder.

To facilitate identification of patients for which treatment according to the disclosure is indicated, a variety of screening methods are known and widely used in the art. Patients presenting with symptoms of an existing psychiatric disorder may be identified by conventional psychiatric evaluation methods. To identify patients at risk for developing the psychiatric disorder, various screening methods are available. Markers can be useful for determining prognostic and/or treatment-related variables. Prognostic variables are those variables that serve to predict the risk of developing the disease. The utility of specific markers for screening and diagnosis depends on the nature and activity of the marker in question. The presence of certain genetic markers may be predictive of a genetic predisposition for the genetic disorder.

As noted above, for the treatment or prevention of psychiatric disorders, the methods of the disclosure involve administering a therapeutically effective amount of an oxytocin releasing compound to a patient in combination or alternation with psychotherapy. Agonists of melanocortin receptors, in particular MC3 and 4, are shown to release oxytocin.

Depression

The most common of these psychological conditions is depression, which ranks first among all causes of disability in the United States and second after heart disease, as a cause of healthy years lost to premature mortality and disability (Regier et al., Arch Gen Psychiatry 45:977 (1988). Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual must have a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Studies have shown that antidepressant drug therapy combined with psychotherapy appears to have better results than either therapy alone (Elkin et al., Arch Gen. Psychiatry 46:971 (1989). Medications used include, but are not limited to, tricyclic antidepressants, monoamine oxidase inhibitors, selective serotonin re-uptake inhibitor (SSRIs), and some new antidepressant drugs such as bupropion, reboxetine, trazodone, venlafaxine, and mitrazapine. Antipsychotic medications are needed for patients suffering from more severe forms of psychotic symptoms, such as delusions or hallucinations. Types of psychotherapy that have proven to be particularly effective for treating depression include interpersonal therapy, group therapy, and cognitive behavioral therapy.

Alternative therapeutic methods include the use of herbal products for management of chronic conditions, such as psychiatric disorders, including anxiety and depression. In addition, St. John's Wort (*hypericum*) has recently gained popularity as an adjunct antidepressant in the United States. The National Institute of Health has recently sponsored a *Hypericum* Clinical Trial comparing 50 to 150 mg/day of sertraline (Zololoft), 900 to 1800 mg/day of St. John's Wort, and placebo in 300 patients with major depression. The conclusion of the study was St. John's Wort was no more effective for treating major depression of moderate severity than a placebo (NIH News Release, Apr. 9, 2002). Side effects of St. John's Wort are mild and primarily include gastrointestinal symptoms and fatigue. Therefore, there is a need in the art for alternative treatments, which are more effective and are associated with fewer side effects for treating major depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are often due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression" wherein the individual is mildly depressed most of the time, with periodic symptoms of major depression.

The least severe form of depression is a depressed mood. This is an emotional state dominated by feelings of sadness, gloominess, or emptiness, which may be associated with lack of energy. Depressed moods are usually temporary responses to an unhappy or stressful event. Treatments for such conditions are the same as discussed above in treatments for mild depressive disorders.

Bipolar Disorders

Bipolar disorder is a chronic disease affecting over 2 million Americans at some point in their lives. Bipolar disorder affects men and women equally and appears between the ages of 15 and 25. As opposed to unipolar major depression, the incidence of bipolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of bipolar disorder, type I and type II. The type I (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, and little need for sleep. In the depressive phase, there is loss of self-esteem, withdrawal, sadness, and a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and antidepressants (e.g., bupropion) is effective for controlling bipolar disorders. Even though lithium is effective in controlling manic and depressive relapses, careful medical supervision along with maintaining salt intake, avoiding nonsteroidal anti-inflammatory drugs, and undertaking weight-reduction diets are all required in order to reduce possible renal failure. Valproate also is characterized by severe side effects including nausea, vomiting, anorexia, heartburn, and diarrhea. Finally, the use of antidepressants for suppressing bipolar disorder must also be carefully monitored in order to achieve full symptomatic remission. Therefore, safer therapeutic methods are needed in the art in order to reduce the severe side effects associated with current treatments of bipolar disorders.

Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like bipolar disorders, though often not as aggressively. Thus, safer treatments are needed in the art.

Anxiety Disorders

Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, and nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines, which facilitate the actions of gamma-aminobutyric acid (GABA), the major inhibitory neurotransmitter in the nervous system, are the most effective in severe cases of anxiety. In addition to these treatments, use of antidepressants such as imipramine and the selective serotonin re-uptake inhibitor (SSRI) paroxetine have been shown to produce antianxiety benefit to anxiety patients (Rocca et al., Acta Psychiatr Scand 95:444 (1997)). Treatment with benzodiazepines, however, is accompanied by fatigue, drowsiness, and unsteadiness. After successive treatments with benzodiazepines, patients often develop dependence to the drug and, therefore, careful medical monitoring is required. Thus, there is a need in the art for treatments that provide less drug dependence along with a reduction in side effects and costs.

Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred. The prevalence rate of panic attacks in the population is as high as 1.5 to 5% (Cruz, et al). Panic disorder can occur in children, but the average age of onset is 25 years old. Panic disorder affects middle-aged and older adults as well. Studies have shown that women are 2 to 3 times more likely to be affected (Cruz, et al.).

Symptoms of panic disorder include shortness of breath, dizziness, palpitations, trembling, sweating, choking, nausea, numbness, chest pain, hot flashes or chills, fear of dying, fear of losing control, and fear of going insane. Symptoms of agoraphobia include anxiety about being in places where escape might be difficult, fear of being alone, fear of losing control in a public place, feeling of helplessness, and feelings of detachment. Treatments for both disorders are similar to treatment of anxiety. Antidepressant medicines are effective for treatment of many people with panic disorder and agoraphobia including SSRIs such as Paxil. Behavior therapies are also used in conjunction with drug therapy including relaxation techniques, pleasant mental imagery, and cognitive behavioral therapy to restructure distorted and harmful interpretations of particular situations.

Other Psychological Disorders

Attention Deficit Disorder (ADD) is the most commonly diagnosed psychological disorder of childhood, affecting 3% to 5% of school aged children. Symptoms include developmentally inappropriate levels of attention, concentration, activity, distractibility, and impulsivity. There are three sub-categories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type. Despite much progress in the diagnosis and treatment of ADD, the treatment for this disorder remains highly controversial. While the cause of attention deficit disorder is unknown, scientists have determined a neurological basis for the disease and genes have been identified that are thought to be involved in ADD.

The most effective treatment strategy for ADD is using psychotropic medications such as Dexedine (dextroamphetamine), Ritalin (methylphenidate), and Cylert (magnesium pemoline). Antidepressants (such as amitriptyline or fluoxetine), tranquilizers (such as thionidazine), alpha-adrenergic agonist (clonidine), and caffeine have also been tried to treat ADD. The disadvantage of these drugs is the lack of long term information on the affect these drugs have on the cognitive and emotional development of ADD children. In addition, medications such as antidepressants, tranquilizers, and caffeine have met with little success. A significant amount of research has been carried out studying psychological therapeutic treatments such as contingency management (e.g. time out), cognitive-behavioral treatment (e.g. self monitoring, verbal self instruction, problem solving strategies, and self reinforcement), parent counseling, and individual psychotherapy. Studies using these techniques have yielded mixed results and no studies have been carried out combining psychological interventions with stimulant medications. Therefore, parents are directed to manage the symptoms and direct the child's energy to constructive and educational paths.

Sleep Disorders

Another secondary effect of depression and other psychological conditions is sleep disorders. A sleep disorder is a disruptive pattern of sleep that may include difficulty: falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (insomnia, e.g.), problems with staying awake (sleep state misperception, e.g.), problems with adhering to a regular sleep schedule (hypersomnias such as narcolepsy, e.g.), and sleep disruptive behaviors (sleep walking, e.g.). Both insomnia and sleep disruptive behaviors could be direct results of a patient suffering from a psychological disorder such as depression or anxiety.

Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic. Common factors associated with insomnia are depression, anxiety, stress, illness, caffeine, abuse of alcohol, medication, illness, physical discomfort, and counterproductive sleep habits such as early bedtimes and daytime napping. Treatment of insomnia is related to the cause. If there is an obvious physical or psychological cause (such as depression), it is the first focus, of treatment.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep. Again, treatment of sleep disruptive behaviors is often related to the cause. If there is an obvious physical or psychological cause, it is the first focus of treatment.

Autism

Autism Spectrum Disorder, including Asperger's Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypes and self-stimulatory behaviors. The social deficit dimension involves deficits in reciprocal social interactions, lack of eye contact, diminished ability to carry on conversation, and impaired daily interaction skills. The cognitive deficits can include language abnormalities.

Autism, outside of its debilitating effect on afflicted individuals, has become an increasing social burden. It is estimated that some 500,000 to 1,500,000 people in the U.S. today have autism or some form of related pervasive developmental disorder. The high incidence rate makes autism one of the most common developmental disabilities. California has found an alarming increase in the number of requests for services for autistic children. The number of requests for treatment between 1987 and 1998 has increased 273%. In addition, the US Department of Education has reported a 556% increase in the number of autistic children in the years from 1991 to 1997. Unfortunately, there are currently few treatment options for children and adults suffering from autism or disorders with similar behavioral characteristics.

PTSD

In one aspect of the present disclosure, the psychiatric disorder to be treated is PTSD. Posttraumatic stress disorder (PTSD) is defined by DSM-IV as an anxiety disorder that an individual may develop following exposure to a traumatic event, and is characterized by (1) reexperiencing the traumatic event, such as recurrent nightmares, intrusive recollections of the event, flashbacks, physiological and psychological responses to internal or external cues relating to the event, etc; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilence, irritability, difficulty sleeping, etc. In the US the lifetime prevalence of PTSD is at least 1%, and in high-risk populations, such as combat veterans or victims of criminal violence, prevalence is reported to be between 3 and 58%; PTSD is therefore of considerable public health concern.

Therapy

The methods of the disclosure encompass the use of any type of psychotherapy that is suitable for the particular psychiatric disorder for which the individual is undergoing treatment, and may be conducted in one or more sessions. Suitable methods of psychotherapy include behavior psychotherapy such as exposure-based psychotherapy, cognitive psychotherapy including cognitive training and psychodynamically oriented psychotherapy (see, for example, Foa (2000) J. Clin. Psych. 61 (suppl. 5):43-38). This includes Applied Behavioral Analysis which is commonly used in the treatment of autism spectrum disorders. This also includes therapies assisted by computer technologies. Exposure based psychotherapy include for example, systematic desensitization, flooding, implosive therapy, and extinction-based therapy. Such psychotherapy modalities are well known to one skilled in the art of psychiatry. "Psychotherapy" refers broadly to forms of psychiatric treatment which employ specialized communication techniques practiced by a properly trained physician, counselor, or clinician for the purpose of curing or reducing or alleviating a behavioral disorder of a patient and improving the patient's emotional, social, and/or mental health.

One method of psychotherapy specifically contemplated is the use of virtual reality (VR) exposure therapy to treat a psychiatric disorder using the combination therapy protocol of the disclosure. VR exposure therapy has been used to treat a variety of disorders including anxiety disorders such as the fear of heights (Rothbaum and Hodges (1999) Behav. Modif 23(4):507-25), as well as specific phobias, eating disorders, and PTSD (Anderson et al. (2001) Bull. Menninger Clin. 65(1):78-91). Because of the prevalence of psychological conditions in the general population and the successful use of VR therapy to treat certain conditions such as PTSD in, for example, Vietnam veterans (Rothbaum et al. 30 (1999) J. Trauma Stress 12(2):263-71) or rape victims (Rothbaum et al. (2001) J. Trauma Stress 14(2):283-93), one embodiment of the present disclosure specifically contemplates the use of such VR exposure psychotherapy in combination with a oxytocin releasing compound as described elsewhere herein to treat a psychological condition. Applied Behavior Analysis (ABA)

ABA refers to using behavioral learning to modify overt behaviors. Behavior analysts focus on the observable relationship of behavior to the environment. By functionally assessing the relationship between a targeted behavior and the environment, the methods of ABA are used to change that behavior, i.e., behavioral intervention methods and cues by which humans adapt and maintain behavior.

Within certain embodiments, the disclosure relates to using methods of ABA in combination with oxytocin-releasing agents to treat people with developmental disabilities, such as autism spectrum disorders. Other developmental disabilities include, but are not limited to, AIDS prevention, conservation of natural resources, education, gerontology, health and exercise, industrial safety, language acquisition, littering, medical procedures, parenting, seatbelt use, mental disorders, sports, and zoo management and care of animals.

Because both desirable and undesirable behaviors are learned through interactions with the social and physical environment, functional behavior assessment (FBA) is used to identify the type and source of reinforcement for challenging behaviors as the basis for intervention efforts designed to decrease the occurrence of these behaviors. Functional behavior assessments typically include the steps of gathering of information via indirect and descriptive assessment; interpreting information from indirect and descriptive assessment and formulation of a hypothesis about the purpose of problem behavior; testing of a hypothesis using a functional analysis; and developing intervention options based on the function of problem behavior. Within certain embodiments, the disclosure relates to using oxytocin-releasing agents in combination with intervention options which may include chaining, prompting (cueing), subsequently fading or thinning the use cues, shaping, i.e., gradually modifying the existing behavior into the desired behavior, and modeling.

Typical cues include verbal, e.g., utilizing a vocalization to indicate the desired response; visual, e.g., picture; gestural, e.g., utilizing a physical gesture to indicate the desired response; positional, e.g., a target item is placed closer to the individual; and physically manipulating the individual to produce the desired response. There are many degrees of physical prompts, e.g., hand-over-hand and a slight tap to initiate movement.

The oxytocin releasing compound may be administered to the patient prior to, during or after the psychotherapy session. It is preferably administered within about 24 hours prior to or following the session of psychotherapy, more preferably within about 24 hour prior to initiating psychotherapy, and even more preferably within about 12 hours prior to initiating psychotherapy. A full course of treatment of psychiatric disorder entails at least one session of this combination therapy protocol.

The oxytocin releasing compound may be administered in a composition suitable for oral, rectal, topical, and parenteral (including subcutaneous, intramuscular, and intravenous) administration, although the most suitable route in any given case will depend on the particular subject, and nature and severity of the conditions for which the active ingredient is being administered. The pharmaceutical compositions may be conveniently presented in unit dosage form and prepared by any of the methods well known in the art of pharmacy.

Administration

The oxytocin-releasing agent is administered in a therapeutically effective amount, which is that amount that provides improved therapeutic benefit relative to that achieved by psychotherapy alone. Dosage levels from about 0.001 mg/kg to about 140 mg/kg of body weight per day are useful for the purpose of the present disclosure or about 0.05 mg to about 7 g per patient per day. Alternatively, dosage levels from about 0.01 mg to 50 mg of the compound per kilogram of body weight per day, or alternatively about 0.5 mg to about 2.5 g per patient per day.

The amount of active ingredient that may be combined with the carrier materials to produce a single dosage form will vary depending upon the subject treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The oxytocin releasing compound described above may be administered, as appropriate, with a carrier and/or one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a oxytocin releasing compound may also be prepared in powder or liquid concentrate form. Further, the compound of this disclosure can be utilized in combination with other therapeutic compounds. In particular, the combinations of the oxytocin releasing compound of this disclosure can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

The oxytocin releasing compound may be administered with capsules, cachets or tablets each containing 1 mg, 5 mg, 25 mg, 50 mg, 100 mg, 200 mg, 300 mg, 400 mg, or 500 mg of the active ingredient of the compound of the present application, or a pharmaceutically acceptable salt thereof, administered prior to, during or after a session.

A subject undergoing treatment with the methods of the disclosure exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington D.C.)), which is herein incorporated by reference. The efficacy of the methods of the disclosure can be assessed using any clinically recognized assessment method for measuring a reduction of one or more symptoms of the particular psychiatric disorder. Examples of such assessment methods are described in, for example, in Experiment 7 of PCT Application WO02/078629. "Alleviation of symptoms," in the context of a behavioral disorder, refers to improvement in the social or psychological function or health of a patient, as evaluated by any measure accepted in the art. Preferably, "alleviation of symptoms" is a clinically recognizable decrease in symptoms described in DSM-IV-TR (American Psychiatric Association, 2000). The psychosocial function of a patient may be evaluated using standard measures provided in DSM-IV-TR (American Psychiatric Association, 2001), such as the Global Assessment of Functioning Scale and the Social and Occupational Functioning Assessment Scale.

Pharmaceutical Compositions

The oxytocin releasing compound is typically formulated with a pharmaceutically acceptable carrier and administered in a therapeutically effective amount, according to the intended use and the desired results. For example, a therapeutically effective amount can be an amount sufficient to reduce the number of therapy visits needed to treat a particular condition, or to enhance the patient's self-reported happiness level, or to otherwise alleviate the symptoms of a psychiatric condition.

In practice, the oxytocin releasing compound can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the oxytocin releasing compound may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

For use within the present disclosure, oxytocin releasing compound preparations are provided for intranasal, intrapulmonary, intramuscular, intravenous, transmucosal or transdermal administration that contain a oxytocin releasing compound in a biologically suitable, liquid or solid carrier. Typically, oxytocin releasing compound preparations contain between about 0.001 and 50 milligrams per milliliter and preferably about 0.1 to 50 mL of liquid carrier or per gram of solid carrier.

As used herein, a "therapeutically effective amount" is an amount of the compound which, depending on the selected mode, frequency and duration of administration, and the desired results. A therapeutically effective amount for the treatment of a psychiatric disorder is one that, depending on the selected mode, frequency and duration of administration, inhibits the occurrence or recurrence of the psychiatric disorder in the patient or alleviates one or more symptoms of the disorder in the patient. Effective amounts to inhibit the occurrence or recurrence of the psychiatric disorder in a patient are prophylactic dosages preferably administered in small amounts over a prolonged course of preventive therapy to patients at risk of developing the disorder. Determination of effective dosages in this case is typically based on human clinical trials and is approximated by determining effective dosages that significantly reduce the occurrence or incidence of the psychiatric disorder in model patients and administration protocols. The time to pharmacokinetic and clinical steady state following oxytocin releasing compound administration is readily determined depending on the mode, frequency and duration of administration, as discussed above. It is therefore a routine matter to determine an appropriate concentration and dose to administer an effective amount (e.g., intranasally effective, transdermally effective, intravenously effective, or intramuscularly effective) of oxytocin releasing compound to elicit a desired response.

The actual dosage will of course vary according to factors such as the disease state, age, and weight of the individual, and the ability of oxytocin releasing compound to elicit a desired response in the individual. Dosage regimens may be adjusted to provide an optimum therapeutic response. A therapeutically effective amount is also one in which any toxic or detrimental side effects of the oxytocin releasing compound are outweighed by therapeutically beneficial effects. A non-limiting range for a therapeutically effective amount of oxytocin releasing compound is 0.001 ug/kg-10 mg/kg, preferably between about 0.001 and 5 mg/kg, although dosages within this range can be achieved by multiple administrations, e.g., multiple administrations per day, daily or weekly administrations. Per administration, it is desirable to administer at least one-tenth of a microgram of oxytocin releasing compound, preferably between 10 ug and 5.0 mg. It is to be further noted that dosage values may vary with the severity of the condition to be alleviated. In addition, for any particular subject, specific dosage regimens should be adjusted over time according to the individual need and professional judgment of the person administering or supervising the administration of the oxytocin releasing compound compositions.

Dosage may be varied by the attending clinician to maintain serum levels at a desired level, for example between 1 and 50 nanomoles per liter. Human dosage necessary to achieve circulating serum levels similar to those achieved in a model rat system under standard conditions tend to be about 30 times the model dosage, although this will vary with the metabolism of individual patients. Dosage should also be adjusted based on the release rate of the administered formulation, e.g., nasal spray versus powder, sustained release oral or injected particles, transdermal formulations, etc. To achieve the same serum concentration level, for example, particles with a release rate of 5 nanomolar (under standard conditions) would be administered at about twice the dosage of particles with a release rate of 10 nanomolar (under standard conditions). A non-limiting range for a therapeutically effective amount of oxytocin releasing compound is 0.001 ug/kg-10 mg/kg, preferably between about 0.001 mg and 5 mg/kg, although dosages within this range can be achieved by multiple administrations, e.g., multiple administrations per day, daily or weekly administrations. Per administration, it is desirable to administer at least one-tenth of a microgram of oxytocin releasing compound, preferably between 10 ug and 5.0 mg. In general, a dosage of between about 0.05-250 mg per 50 kg of body weight, more preferably between about 0.1 and 25 mg, may be selected. In unit dosage form (e.g., a unit dosage delivered as a single nasal spray, injection, topical application, etc.), a total amount of oxytocin releasing compound is preferably selected to be at least about 0.1 mg, 0.5 mg, 1.0 mg 2.0 mg, 5.0 mg or greater. The dosage selected preferably maintains serum concentration below 50 nanomoles per liter, preferably between 1.0 nanomoles per liter and 10, 15 or 25 nanomoles per liter depending on patient's response.

Therapeutic compositions can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

As used herein, "pharmaceutically acceptable carrier" includes any and all solvents, dispersion media, coatings, antibacterial and antifungal agents, isotonic and absorption enhancing or delaying agents, and other excipients or additives that are physiologically compatible. Preferably, the carrier is suitable for intranasal, intravenous, intramuscular, subcutaneous, parenteral, oral, transmucosal or transdermal administration. Depending on the route of administration, the active compound may be coated in a material to protect the compound from the action of acids and other natural conditions which may inactivate the compound.

Thus, the pharmaceutical compositions of this disclosure may include a pharmaceutically acceptable carrier and a compound or a pharmaceutically acceptable salt of a compound of the Examples. The compounds or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this disclosure may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions of the present disclosure suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present disclosure can be in a form suitable for topical use such as, for example, an aerosol, cream, ointment, lotion, dusting powder, or the like. Further, the compositions can be in a form suitable for use in transdermal devices prepared via conventional processes. As an example, a cream or ointment is prepared by mixing hydrophilic material and water, together with about 5 wt % to about 10 wt % of the compound, to produce a cream or ointment having a desired consistency.

Pharmaceutical compositions of this disclosure can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In certain embodiments of the disclosure, the oxytocin releasing compound is administered in a time release formulation, for example in a composition which includes a slow release polymer, or by depot injection. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparing such formulations are generally known to those skilled in the art (See, e.g., Sustained and Controlled Release Drug Delivery Systems, J. R. Robinson, ed., Marcel Dekker, Inc., New York, 1978, incorporated herein by reference). Particularly preferred formulations include controlled-release compositions such as are known in the art for the administration of leuprolide (trade name: LUPRON™), e.g., microcapsules (U.S. Pat. Nos. 4,652,441 and 4,917,893, each incorporated herein by reference), injectable formulations (U.S. Pat. No. 4,849,228, incorporated herein by reference), lactic acid-glycolic acid copolymers useful in making microcapsules or injectable formulations (U.S. Pat. Nos. 4,677,191 and 4,728,721, each incorporated herein by reference), and sustained-release compositions for water-soluble peptides (U.S. Pat. No. 4,675,189, incorporated herein by reference). A long-term sustained release implant also may be used. These can be readily constructed to deliver therapeutic levels of oxytocin releasing compound for at least 30 days, preferably 60 days or longer. Long-term sustained release implants are well known to those of ordinary skill in the art and can incorporate some of the absorption delaying components described above.

In alternate embodiments, oxytocin releasing compound may be orally or rectally administered with an inert diluent or an edible carrier. The compound may thus be enclosed in a hard or soft shell gelatin capsule, compressed into tablets, or incorporated directly into the subject's diet. For oral therapeutic administration, oxytocin releasing compound may be incorporated with excipients and used in the form of ingestible tablets, buccal tablets, troches, capsules, elixirs, suspensions, syrups, wafers, and the like. The percentage of compound in these compositions and preparations may, of course, be varied. The amount of compound in such therapeutically useful compositions is such that a suitable dosage will be obtained. For oral or rectal administration, oxytocin releasing compound can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms. Solid delivery vehicles may contain oxytocin releasing compound in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols. As further forms, one can use plug capsules, e.g., of hard gelatin, as well as dosed soft-gelatin capsules comprising a softener or plasticizer, e.g. glycerine. Alternatively, liquid dosage forms for delivering oxytocin releasing compound to mucosal surfaces include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

To administer oxytocin releasing compound in a stable form within the methods of the disclosure, it may be necessary to coat the compound with, or co-administer the compound with, a material to prevent its inactivation. In this context oxytocin releasing compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7:27, 1984, incorporated herein by reference). Pharmaceutically acceptable carriers include sterile aqueous solutions or dispersions and sterile powders for the extemporaneous preparation of sterile injectable or aerosol solutions or dispersible powder formulations. The use of such media and agents for pharmaceutically active substances is well known in the art. Except insofar as any conventional media or agent is incompatible with the active compound or yields unacceptable toxic or other adverse side effects, use thereof in the pharmaceutical compositions of the disclosure is contemplated. In one embodiment, supplementary active compounds, including hormonal therapeutic and chemotherapeutic agents useful against breast cancer, can also be incorporated into the compositions of the disclosure. In another embodiment, the supplementary active compounds include antidepressants, such as selective serotonin reuptake inhibitors (e.g., fluvoxamine, paroxetine, sertraline and paroxetine) or serotonin reuptake inhibitors (e.g., clomipramine).

In more detailed aspects of the disclosure, the oxytocin releasing compound is stabilized to extend its effective half-life following delivery to the subject, particularly for extending metabolic persistence in an active state within an extracellular compartment (e.g., in the bloodstream, at a mucosal surface, or within a connective tissue compartment or fluid-filled body cavity). For this purpose, the oxytocin releasing compound may be modified by chemical means, e.g., chemical conjugation, N-terminal capping, PEGylation, or recombinant means, e.g., site-directed mutagenesis or construction of fusion proteins, or formulated with various stabilizing agents or carriers. The oxytocin releasing compound can also be modified with other appending groups, such as peptides, or agents facilitating transport across the cell membrane (see, e.g., Letsinger et al., Proc. Natl. Acad. Sci. USA 86:6553-6556, 1989; Lemaitre et al., Proc. Natl. Acad. Sci. USA 84:648-652, 1987; International Patent Publication WO 88/09810) or blood-brain barrier (see, e.g., International Patent Publication WO 89/10134). Numerous reports in the literature describe the potential advantages of PEGylated proteins, which include their increased resistance to proteolytic degradation, increased plasma half-life, increased solubility and decreased antigenicity and immunogenicity (Nucci et al., Advanced Drug Delivery Reviews 6:133-155, 1991; Lu et al., Int. J. Peptide Protein Res. 43:127-138, 1994, each incorporated herein by reference). A number of proteins, including L-asparaginase, strepto-kinase, insulin, and interleukin-2 have been conjugated to a poly(ethyleneglycol) (PEG) and evaluated for their altered biochemical properties as therapeutics (see, e.g., Ho et al., Drug Metabolism and disposition 14:349-352, 1986; Abuchowski et al., Prep. Biochem. 9:205-211, 1979; and Rajagopaian et al., J. Clin. Invest. 75:413-419, 1985, each incorporated herein by reference). Although the in vitro biological activities of PEGylated proteins may be decreased, this loss in activity is usually offset by the increased in vivo half-life in the bloodstream (Nucci, et al., Advanced Drug Delivery Reviews 6:133-155, 1991, incorporated herein by reference).

Several procedures have been reported for the attachment of PEG to proteins and peptides and their subsequent purification (Abuchowski et al., J. Biol. Chem. 252:3582-3586, 1977; Beauchamp et al., Anal. Biochem. 131:25-33, 1983, each incorporated herein by reference). Lu et al., Int. J. Peptide Protein Res. 43:127-138, 1994 describe various technical considerations and compare PEGylation procedures for proteins versus peptides (see also, Katre et al., Proc. Natl. Acad. Sci. USA 84:1487-1491, 1987; Becker et al., Makromol. Chem. Rapid Commun. 3:217-223, 1982; Mutter et al., Makromol. Chem. Rapid Commun. 13:151-157, 1992; Merrifield, R. B., J. Am. Chem. Soc. 85:2149-2154, 1993; Lu et al., Peptide Res. 6:142-146, 1993; Lee et al., Bioconjugate Chem. 10:973-981, 1999, Nucci et al., Adv. Drug Deliv. Rev. 6:133-151, 1991; Francis et al., J. Drug Targeting 3:321-340, 1996; Zalipsky, S., Bioconjugate Chem. 6:150-165, 1995; Clark et al., J. Biol. Chem. 271: 21969-21977, 1996; Pettit et al., J. Biol. Chem. 272:2312-2318, 1997; Delgado et al., Br. J. Cancer 73:175-182, 1996; Benhar et al., Bioconjugate Chem. 5:321-326, 1994; Benhar et al., J. Biol. Chem. 269:13398-13404, 1994; Wang et. al., Cancer Res. 53:4588-4594, 1993; Kinstler et al., Pharm. Res. 13:996-1002, 1996, Filpula et al., Exp. Opin. Ther. Patents 9:231-245, 1999; Pelegrin et al., Hum. Gene Ther. 9:2165-2175, 1998, each incorporated herein by reference).

In addition to PEGylation, the compounds can be modified to enhance circulating half-life by shielding the protein via conjugation to other known protecting or stabilizing compounds, or by the creation of fusion proteins with the oxytocin releasing compound proteins or peptides and other proteins such as immunoglobulin chains. These modifications will decrease the degradation, sequestration or clearance of the oxytocin releasing compounds and result in a longer half-life of the protein, e.g., in the nasal sinus, lung, circulatory system, or synovium.

The therapeutic compositions of the disclosure typically must be sterile and stable under all conditions of manufacture, storage and use. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like. Prolonged delivery of oxytocin releasing compound in various compositions of the disclosure can be brought about by inclusion in the composition of agents delaying absorption, for example, aluminum mono sterate hydrogels and gelatin.

When controlled release formulations are desired, controlled release binders suitable for use in accordance with the disclosure include any biocompatible controlled-release material which is inert to the active ingredient and which is capable of incorporating the oxytocin releasing compound. Numerous such materials are known in the art. Preferred controlled-release binders are materials which are metabolized slowly under physiological conditions following their subcutaneous or intramuscular injection in mammals (i.e., in the presence of bodily fluids which exist there). Appropriate binders include but are not limited to biocompatible polymers and copolymers previously used in the art in sustained release formulations. Such biocompatible compounds are non-toxic and inert to surrounding tissues, e.g., following subcutaneous or intramuscular injection, and do not trigger significant adverse effects such as immune response, inflammation, or the like. They are metabolized into metabolic products which are also biocompatible and easily eliminated from the body. For example, a polymeric matrix derived from copolymeric and homopolymeric polyesters having hydrolysable ester linkages may be used. A number of these are known in the art to be biodegradable and to lead to degradation products having no or low toxicity. Typically, such preferred polymers are polyglycolic adds (PGA) and polylactic acids (PLA), poly(DL-lactic acid-co-glycolic acid)(DL PLGA), poly(D-lactic acid-coglycolic acid)(D PLGA) and poly(L-lactic acid-co-glycolic acid)(L PLGA). The preferred ratio for lactic acid and glycolic acid polymers in polyo(lactic acid-co-glycolic acid) is in the range of 100:0 (i.e. pure polylactide) to 50:50. Other useful biodegradable or biodegradable polymers include but are not limited to such polymers as poly(epsilon-caprolactone), poly(epsilon-aprolactone-CO-lactic add), poly(epsilon.-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e. L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof.

In some embodiments of the disclosure, the oxytocin releasing compound is administered by topical delivery to a mucosal surface of the patient, preferably via intranasal delivery in the form of an aerosol spray or powder. According to this aspect of the disclosure, oxytocin releasing compound is delivered in an intranasally effective amount, preferably in a selected volume of administered spray or powder, to achieve prophylaxis or treatment of a psychiatric disorder or social condition. In related aspects of the disclosure, novel pharmaceutical compositions are provided for intranasal delivery that incorporate oxytocin releasing compound in a powder or aqueous formulation for intranasal delivery. Intranasal administration of oxytocin releasing compound is preferred for a variety of reasons. This method allows self-administration of treatment by patients, provided that sufficient safeguards are in place to control and monitor dosing and side effects. Nasal administration also overcomes certain drawbacks of other administration forms, such as injections, that are painful and expose the patient to possible infections and may present drug bioavailability problems.

Compositions according to the present disclosure are preferably administered in solution as a nasal spray and may be dispensed as a spray by a variety of methods known to those skilled in the art. Systems for intranasally dispensing liquids as a spray are well known (see, e.g., U.S. Pat. No. 4,511,069, incorporated herein by reference). Preferred nasal spray solutions comprise oxytocin releasing compound in a liquid carrier that optionally include a nonionic surfactant for enhancing absorption of the drug and one or more buffers or other additives to minimize nasal irritation. In addition, any of the enhancers and other excipients used to delivery peptides across absorptive mucosae can be included (see Sayani, A. P. and Chien, Y. W., Critical Reviews in Therapeutic Drug Carrier Systems 13:85-184, 1996, incorporated herein by reference). In some embodiments of the present disclosure, the nasal spray solution further comprises a propellant. The pH of the nasal spray solution is preferably between pH 3.0 and 8.0. For intranasal administration, compositions which improve the absorption of nasally administered oxytocin releasing compound and reduce nasal irritation, especially when used in a chronically administered treatment protocol, are desirable. In this context, the utilization of surface-active agents to enhance absorption of polypeptide therapeutics has been previously demonstrated. For example, Hirai and coworkers (Hirai, et al., Int. J. Pharmaceutics 1:173-184, 1981; G.B. Patent specification 1 527 605, each incorporated herein by reference). However, nasal administration of drugs enhanced by surfactants may be accompanied by nasal irritation, including stinging, congestion and rhinorrhea. Thus, compositions which enhance absorption through the nasal mucosa with reduced irritation are desirable. To achieve this goal, a combination of surfactants may be used. Nonionic surfactants such as nonoxynol-9, laureth-9, poloxamer-124, octoxynol-9 and lauramide DEA are particularly useful in the practice of the present disclosure. Nonoxynol-9 (N-9) is an ethoxylated alkyl phenol, the polyethyleneoxy condensate of nonylphenol with 9 mols of ethylene oxide. This surfactant has been used in detergent products and is sold under trade names, such as, SURFONIC™ N-95 (Jefferson), NEUTRONYX™ 600 (Onyx) and IGEPAL™ CO-630 (GAF). N-9 is considered to be a hard detergent. N-9 has also been used as a spermatocide (The Merck Index, 10th Edition, Entry 6518). To minimize irritation attributed to employment of surfactants, one or more anti-irritant additives are included in the oxytocin releasing compound solution. In one example, polysorbate-80 has been shown to reduce the irritation caused by intranasally administered drugs where delivery was enhanced by use of a nonionic surfactant (See, e.g., U.S. Pat. No. 5,902,789, issued to Stoltz on May 11, 1999, incorporated herein by reference).

Alternative means of intranasal oxytocin releasing compound administration are provided by the use of ion exchange resins or adsorbent resin powders as carriers. Use of these materials is also adaptable for oxytocin releasing compound administration via oral, percutaneous, gastrointestinal, rectal, or subcutaneous routes. For intranasal use, these materials minimize irritation to the nasal mucosa and deliver oxytocin releasing compound in a stable form and with efficient absorption. Thus, methods and compositions are provided wherein oxytocin releasing compound is formulated with an ion exchange resin or an adsorbent resin powder as a carrier which effectively delivers the oxytocin releasing compound to, and supports its transfer across, the surface of the nasal mucosa for absorption into the general circulation. The method used for compounding oxytocin releasing compound with the carrier and other related disclosure is provided in U.S. Pat. No. 5,942,242, issued to Muzushima et al. on Aug. 24, 1999 (incorporated herein by reference). Such methods include: (1) preparing a suspension by adding an ion exchange resin or adsorbent resin powder to a vaccine solution or suspension; (2) mixing dried oxytocin releasing compound with an ion exchange resin or adsorbent resin powder by means of a mortar or ball mill while maintaining an appropriate relative humidity; (3) freeze drying a suspension obtained by step (1); and (4) increasing the homogeneity of a mixture of step (2) by adding an organic solvent such as ethanol. Ion exchange resins suitable for use in the present disclosure include: polystyrenes, methacrylic resin, acrylic resins, phenol-formaldehyde resins, cellulose polymers, dextran polymers, and mixtures thereof. Examples of such polymers include, sodium polystyrenesulfonate prepared according to the Pharmacopeia of Japan, calcium polystyrene sulfonate prepared according to the Pharmacopeia of Japan, AMBERLITE® 1RP64, AMBERLITE™ CU-SO, AMBERLITE™ DP-1, and DOWE™ 2, and mixtures thereof, which bear as cation exchange functional groups, sulfonic acid or carboxylic acid, or a salt thereof, e.g., a sodium, potassium, or calcium salt. The anion exchange resins include, for example, quaternary ammonium resin derivatives or, e.g., chloride, salts thereof. Examples of such chloride salts include cholestyramine, AMBERLITE™ 1 RP67, AMBERLITE™ IRA-68, DOWEX™, and mixtures thereof. Examples of adsorbent resins for use within the disclosure include styrenedivinylbenzenes.

To provide an optimal intranasal powder for delivery of carbetocin, a mean particle size of the ion exchange resin or adsorbent resin is not larger than 200 um, preferably 10 to 150 um, and still more preferably 40 to 70 um. The total amount of powdered medicament to be administered into the human nasal cavity as a single dose is preferably approximately 5 to 50 mg, preferably 10 to 30 mg, more preferably 15 to 25 mg. In this case, the total amount is the sum of the amount of carbetocin and carrier as well as any other active ingredients or additives. As for solid medicaments delivered in a liquid suspension (e.g., a carbetocin/resin solid suspended in a liquid carrier), the amount for a single dose is preferably 0.1 to 2.5 ml, preferably 0.2 to 2.0 ml, more preferably 0.3 to 1.5 ml.

To increase both adherence to the nasal mucosa and the stability of nasal powders and solid suspensions, the present disclosure may include a water-soluble polymer powder, such as: polyacrylic acid or polymethacrylic acids or metal salts, such as sodium salt or potassium salts, thereof, with a mean particle size of 0.5 to 200 um, preferably 20 to 100 um; a water-soluble acrylate polymer such as polyacrylamide, having a molecular weight of 30,000 or greater, preferably 50,000 to 10,000,000; carboxyvinyl polymers, methylcelluloses, ethylcelluloses, hydroxymethylcelluloses, hydroxypropylmethylcelluloses, carboxymethylcelluloses, carboxymethylchitin, polyvinylpyrrolidone, polyvinylalcohols, ester gums, polybutene, synthetic hydroxypropyl-starch, synthetic carboxymethyl-starch, synthetic polyvinylethers, and polyethylene oxide, having an average molecular weight of 20,000 to 9,000,000, and preferably 100,000 to 7,000,000; natural polymers such as hyaluronic acid, sodium alginate, gelatin, gluten, carboxymethyl-starch, hydroxypropyl-starch, gum arabic, mannan, dextran, tragacanth, amylopectin, xanthan gum, locust bean gum, casein, polyvinylethers, and pectin; and mixtures thereof.

The instant disclosure also includes kits, packages and multi-container units containing the above described pharmaceutical compositions, active ingredients, and/or means for administering the same for use in the prevention and treatment of a psychiatric or behavioral disorder, as discussed above. Briefly, these kits include a pharmaceutical preparation of oxytocin releasing compound in a biologically suitable carrier optionally contained in a bulk dispensing or unit or multi-unit dosage form. Optional dispensing means may be provided for administering the oxytocin releasing compound, preferably including an intranasal spray applicator. Preferred applicators include pressurized aerosol or hand-pump reservoirs preferably equipped with a nozzle for placement in a nostril of the patient and functional to direct a liquid spray of the oxytocin releasing compound solution therein.

Examples

Melanotan II and Buspirone Facilitate Partner Preference Formation in Prairie Voles.

Social bonding in prairie voles is a complex social cognitive process, which involves the synthesis of social motivation, social information process and social learning. Bonding can be efficiently assayed in the laboratory using a partner preference paradigm (Ahern, 2009). The formation of a partner preference in female prairie voles is dependent on OT (Williams, 1994). In the absence of mating, 24 hrs of cohabitation is typically needed for the development of a partner preference. However, OT administration accelerates partner preference formation to 6 hrs or less. Partner preferences are formed during the cohabitation period through the neural processing of social information, learning and reinforcement. Oxytocin is thought to enhance one or more of these processes. The cohabitation period is analogous to the behavioral therapy sessions used in the treatment of psychiatric disorders. Thus a drug that enhances partner preferences in voles, may also enhance the effects of the behavior therapy session in humans. Melanotan I (MTI) and Melanotan II (MTII), synthetic α-MSH analogues, which act on melanocortin ¾ receptors, and busprione (BUS), a 5-HT1a receptor partial agonist, We administered to female prairie voles and assessed partner preference.

In order to determine whether the effects of stimulating OT release produced long-term changes in social behavior, a second experiment was performed in which prairie voles were treated with MTII, and cohabitated with a partner for six hours. After this brief cohabitation, the pair was separated for one week. Following this separation partner preference formation were assessed, well after the drug was eliminated.

Methods

Subjects were 60 adult (60-90 days of age) sexually naïve ovariectomized female prairie voles from out colony maintained at the Yerkes National Primate Research Center at Emory University. This facility is accredited by the Association for the Assessment and Accreditation of Laboratory Animal Care (AAALAC). Prairie voles in our colony are derived from Illinois field caught stock. Animals were last introduced from the wild in 2008. All animals were weaned at 19-21 days, maintained in same-sex groups of 2-3 under a 14/10 light/dark cycle with a stable environmental temperature of 22° C. with access to food (LabDiet rabbit) and water ad libitum. Cages in our animal colony are regularly changed once a week. All procedures used in this study were approved by the Institutional Care and Use Committee of Emory University.

Partner Preference Test

Female prairie voles were injected intraperitoneally with either Melanotan II (1.10 mg/kg; Sigma Aldrich, St. Louis, Mo.), buspirone (8, 30 mg/kg; Sigma Aldrich, St. Louis, Mo.) or a saline control in a dissolved in a volume of 0.1 ml 0.1% sterile saline. Initial doses were based the doses given to stimulate oxytocin release in the mouse and rat literature. The females were then placed in a clean cage with a sexually experienced male prairie vole. The pairs were cohabitated for six hours and video recorded to monitor for sexual behavior. Females were not receptive and 6 hours of cohabitation without mating typically does not result in a partner preference. The videos were analyzed afterwards for mating attempts and animals that mated were excluded from the study. In the first study, the females were tested for the formation of a partner preference immediately after the cohabitation. In the second study, which tested MTII, the pair were separated for one week, and then tested on the partner preference test. The female was allowed to roam freely in a three-chambered partner preference arena with two male conspecifics, the partner with whom she was cohabitated and an age/experience matched stranger, tethered on either side of the arena. The female was free to move throughout the environment, interact with either male or stay isolated in the central neutral cage. The time the subject spent in side by side contact with no joint motion was scored using the CleverSys Behavioral Analysis System. Total distance moved by the female was also recorded as a measure of general activity. Social bonding as measured by the demonstration of partner preference is used as a measure of general social cognition in the prairie vole.

Total time spent with the partner vs. the stranger was compared for each treatment group using a student's T-test with an alpha value of 0.05. A partner preference was defined as significantly more time spent in immobile social contact with the partner compared to the stranger.

Results

In experiment 1, female prairie voles receiving a low dose of BUS (FIG. 1; p=0.003) or a high dose of MTII (FIG. 1; p=0.003) spent significantly more time with the partner male vs. the stranger male, thus they are considered to have formed a "partner preference". Animals given a control saline injection, a low dose of MTII (FIG. 1; p=0.428), a high dose of BUS (FIG. 1; p=0.392) failed to spend significantly more time with either stimulus animal. No difference from control treatment was seen in the locomotor patterns under any of the drug conditions.

In experiment 2, whether the social attachment would persist after the MT II had been eliminated from the animal was tested. In this case, the pair were separated for one week after the MTII treatment and cohabitation, and then tested on the partner preference test. Saline injected animals failed to prefer the partner over the stranger. However, animals injected with MTII spent significantly more time with the partner than the stranger (p<0.05). Thus MT II facilitated the formation of social memories that endure well after the training (cohabitation).

The invention claimed is:

1. A method of improving reciprocal social interactions during a psychotherapy treatment comprising administering an effective amount of a pharmaceutical composition comprising melanotan II or salt thereof to a subject diagnosed with autism, Asperger syndrome, or an autistic spectrum disorder wherein the administration is about the time period a psychotherapy session is being conducted and the session includes exposure to a reciprocal social interaction.

2. The method of claim 1 wherein the administration is administered during the psychotherapy session.

3. The method of claim 1 wherein the administration is within five minutes of a psychotherapy session.

4. The method of claim 1, wherein the administration is within one hours of a psychotherapy session.

5. The method of claim 1, wherein the administration is within five hours of a psychotherapy session.

* * * * *